United States Patent
Shelly et al.

(10) Patent No.: US 9,463,293 B2
(45) Date of Patent: Oct. 11, 2016

(54) SERVO VENTILATION USING NEGATIVE PRESSURE SUPPORT

(75) Inventors: Benjamin Irwin Shelly, Oakmont, PA (US); Michael Thomas Kane, Harrison City, PA (US); Gregory Delano Matthews, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 570 days.

(21) Appl. No.: 13/521,451

(22) PCT Filed: Dec. 17, 2010

(86) PCT No.: PCT/IB2010/055916
§ 371 (c)(1),
(2), (4) Date: Jul. 11, 2012

(87) PCT Pub. No.: WO2011/086435
PCT Pub. Date: Jul. 21, 2011

(65) Prior Publication Data
US 2013/0047990 A1    Feb. 28, 2013

Related U.S. Application Data

(60) Provisional application No. 61/294,873, filed on Jan. 14, 2010.

(51) Int. Cl.
*A61M 16/00* (2006.01)
*A61M 16/20* (2006.01)

(52) U.S. Cl.
CPC ......... *A61M 16/00* (2013.01); *A61M 16/0003* (2014.02); *A61M 16/0009* (2014.02);
(Continued)

(58) Field of Classification Search
CPC ............. A61M 16/00; A61M 16/003; A61M 16/0051; A61M 16/0057; A61M 16/0063; A61M 16/0066; A61M 16/0069; A61M 16/204; A61M 16/205; A61M 2016/003; A61M 2016/0018; A61M 2016/0033; A61M 2016/0036; A61M 2016/0039; A61M 2016/0041; A61M 2016/1005; A61M 2016/102; A61M 2205/33; A61M 2205/3331; A61M 2205/3334; A61M 2205/3351; A61M 2230/42
USPC ............ 128/204.23, 204.21, 204.26, 204.29, 128/204.18
See application file for complete search history.

(56) References Cited

U.S. PATENT DOCUMENTS

| | | |
|---|---|---|
| 5,044,362 A | 9/1991 | Younes |
| 5,107,830 A | 4/1992 | Younes |

(Continued)

FOREIGN PATENT DOCUMENTS

| | | |
|---|---|---|
| CN | 101014380 A | 8/2007 |
| CN | 101299963 A | 11/2008 |

(Continued)

*Primary Examiner* — Justine Yu
*Assistant Examiner* — Tu Vo
(74) *Attorney, Agent, or Firm* — Michael W. Haas

(57) ABSTRACT

A system for delivering a flow of breathing gas to a patient's airway that includes a gas flow generator and a patient circuit for communicating the flow of gas to the patient's airway. A sensor measures a characteristic associated with the flow of gas, such as flow rate, maximum average inspiratory flow, tidal volume or minute ventilation. A controller determines a first characteristic based on the measured characteristic and provides positive pressure support to the patient if the first characteristic is below a first target and provides a negative support if the first characteristic is above a second target. When the positive pressure support is provided, the pressure provided during inspiration is higher than the pressure provided during expiration. When the negative pressure support is provided, the pressure provided during inspiration is lower than the pressure provided during expiration.

25 Claims, 6 Drawing Sheets

(52) U.S. Cl.
CPC ..... *A61M16/0057* (2013.01); *A61M 16/0066* (2013.01); *A61M 16/0069* (2014.02); *A61M 16/204* (2014.02); A61M 16/0075 (2013.01); A61M 16/20 (2013.01); A61M 16/201 (2014.02); A61M 2016/003 (2013.01); A61M 2016/0015 (2013.01); A61M 2016/0039 (2013.01); A61M 2205/33 (2013.01); A61M 2205/3327 (2013.01); A61M 2205/3331 (2013.01); A61M 2205/3334 (2013.01); A61M 2205/3337 (2013.01); A61M 2205/3355 (2013.01); A61M 2205/3365 (2013.01); A61M 2205/502 (2013.01)

(56) References Cited

U.S. PATENT DOCUMENTS

| | | |
|---|---|---|
| 5,148,802 A | 9/1992 | Sanders |
| 5,203,343 A | 4/1993 | Axe |
| 5,313,937 A | 5/1994 | Zdrojkowski |
| 5,433,193 A | 7/1995 | Sanders |
| 5,458,137 A | 10/1995 | Axe |
| 5,535,738 A | 7/1996 | Estes |
| 5,598,838 A | 2/1997 | Servidio |
| 5,632,269 A | 5/1997 | Zdrojkowski |
| 5,645,053 A | 7/1997 | Remmers |
| 5,794,615 A | 8/1998 | Estes |
| 5,803,065 A | 9/1998 | Zdrojkowski |
| 5,927,274 A | 7/1999 | Servidio |
| 6,029,664 A | 2/2000 | Zdrojkowski |
| 6,087,747 A | 7/2000 | Dhuler |
| 6,105,575 A | 8/2000 | Estes |
| 6,532,959 B1 | 3/2003 | Berthon-Jones |
| 6,532,960 B1 | 3/2003 | Yurko |
| 6,539,940 B2 | 4/2003 | Zdrojkowski |
| 6,609,517 B1 | 8/2003 | Estes |
| 6,626,175 B2 | 9/2003 | Jafari |
| 6,640,806 B2 | 11/2003 | Yurko |
| 6,839,581 B1 | 1/2005 | El-Solh |
| 6,951,217 B2 | 10/2005 | Berthon-Jones |
| 7,011,091 B2 | 3/2006 | Hill |
| RE39,225 E * | 8/2006 | Isaza et al. ............... 128/202.22 |
| 7,168,429 B2 | 1/2007 | Matthews |
| 7,267,122 B2 | 9/2007 | Hill |
| 7,717,110 B2 | 5/2010 | Kane |
| 8,752,546 B2 * | 6/2014 | Acker et al. ............. 128/204.21 |
| 2005/0065567 A1 | 3/2005 | Lee |
| 2005/0076906 A1 * | 4/2005 | Johnson ................... 128/204.21 |
| 2006/0000475 A1 | 1/2006 | Matthews |
| 2006/0070624 A1 | 4/2006 | Kane |
| 2007/0221224 A1 | 9/2007 | Pittman |
| 2008/0000475 A1 | 1/2008 | Hill |
| 2008/0060656 A1 * | 3/2008 | Isaza ........................ 128/207.16 |
| 2008/0302364 A1 | 12/2008 | Garde |

FOREIGN PATENT DOCUMENTS

| | | |
|---|---|---|
| CN | 101500633 A | 8/2009 |
| CN | 101588832 A | 11/2009 |
| EP | 2008581 A2 | 12/2009 |
| JP | 2004526470 A | 9/2004 |
| JP | 2005161068 A | 6/2005 |

* cited by examiner

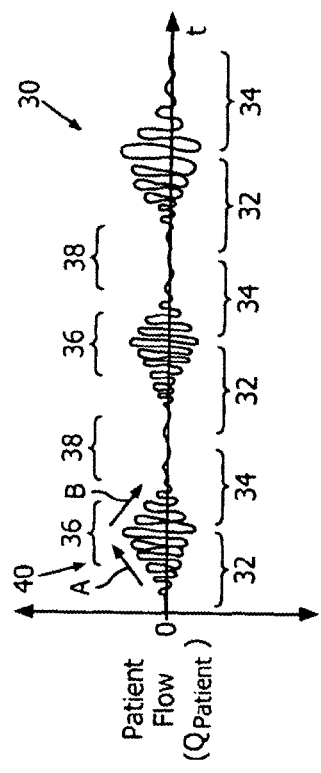

SERVO VENTILATION USING NEGATIVE PRESSURE SUPPORT

CROSS-REFERENCE TO RELATED APPLICATIONS

This patent application claims the priority benefit under 35 U.S.C. §371 of international patent application no. PCT/IB2010/055916, filed Dec. 17, 2010, which claims the priority benefit under 35 U.S.C. §119(e) of U.S. Provisional Application No. 61/294,873filed on Jan. 14, 2010, the contents of which are herein incorporated by reference.

BACKGROUND OF THE INVENTION

1. Field of the Disclosure

The invention relates generally to a method and apparatus for providing a pressure therapy particularly suited to treat Cheyne-Stokes respiration and other breathing disorders, including those commonly associated with congestive heart failure.

2. Description of the Related Art

Congestive heart failure (CHF) patients commonly suffer from respiratory disorders, such as obstructive sleep apnea (OSA) or central apneas. Another such respiratory disorder CHF patients often experience during sleep is known as Cheyne-Stokes respiration. FIG. 1 illustrates a typical Cheyne-Stokes respiration (CSR) pattern 30, which is characterized by rhythmic waxing periods 32 and waning periods 34 of respiration, with regularly recurring periods of high respiratory drive (hyperpnea) 36 and low respiratory drive (hypopnea or apnea) 38. A typical Cheyne-Stokes cycle, generally indicated at 40, lasts about one minute and is characterized by a crescendo (arrow A), in which the peak respiratory flow of the patient increases over several breath cycles, and decrescendo (arrow B), in which the peak respiratory flow of the patient decreases over several breath cycles. The typical Cheyne-Stokes cycle ends with a central apnea or hypopnea following the decrecendo phase. Apneas, hyperpneas, and the abnormal change in the depth and rate of breathing often cause arousals and, thus, degrades sleep quality. This disruption in sleep, as well as the periodic desaturation of arterial oxygen, caused by the CSR cycle stresses the cardio-vascular system and specifically the heart.

The earliest treatment for CSR involved stimulating the respiratory drive by administering Theophyline, caffeine, or 1-3% inspired carbon dioxide to the patient. Although sometimes effective in reducing CSR, the downside of these treatments, which increase the respiratory rate, is that the increase in respiratory rate proportionally increases cardiac and respiratory workload.

Recent work in the treatment of sleep apnea and related breathing disorders has included bi-level positive airway therapy. In bi-level therapy, pressure is applied alternately at relatively higher and lower prescription pressure levels within the airway of the patient so that the therapeutic air pressure is alternately administered at a larger and smaller magnitude. The higher and lower magnitude positive prescription pressure levels are known as inspiratory positive airway pressure (IPAP) and expiratory positive airway pressure (EPAP), respectively. The inspiratory and expiratory pressure are synchronized with the patient's inspiratory cycle and expiratory cycle, respectively.

Some preliminary investigations reveal that cardiac output improves when patients are supported using bi-level pressure therapy. It has also been recognized that CSR can be treated by augmenting respiratory effort with positive pressure support when the CSR pattern is in hypopnea region 38. To accomplish this, it is known to use a ventilator or pressure support system to deliver machine triggered breaths during the hypopnea interval when the patient's own respiratory drive is reduced or not present. In addition, ventilatory efficiency may be decreased when flow is in a hyperpnea region 36. Alternatively, another method of treating CSR is where $CO_2$ is selectively rebreathed during the hyperneic phase of the CSR cycle. However, this method requires additional equipment to be used with the typical ventilator system.

SUMMARY OF THE INVENTION

An aspect provides a system for delivering a flow of breathing gas to an airway of a patient. The system includes a gas flow generator that generates a flow of gas and a patient circuit coupled to the gas flow generator and adapted to communicate the flow of gas to an airway of a patient. The system further includes a sensor associated with the gas flow generator or the patient circuit and adapted to measure a characteristic associated with the flow of gas, such as the flow rate. The system also includes a controller that determines a first characteristic based on the monitored characteristic and that controls the delivery of the flow of gas to the airway of the patient from the gas flow generator via the patient circuit by 1) providing positive pressure support to the patient if the first characteristic is below a first target and 2) providing a negative pressure support to the patient if the first characteristic is above a second target. When the positive pressure support is provided to the patient, the pressure provided to the patient during inspiration is higher than the pressure provided to the patient during expiration. When the negative pressure support is provided to the patient, the pressure provided to the patient during inspiration is lower than the pressure provided to the patient during expiration.

Another aspect provides a method of ventilating a patient. The method includes the steps of delivering a flow of gas to the airway of a patient from a source of breathing gas via a patient circuit, measuring a characteristic associated with the flow of gas (such as flow rate), and determining a first characteristic based on the measured characteristic. The method further includes the steps of controlling delivery of the flow of gas to the patient by 1) providing positive pressure support to the patient if the first characteristic is below a first target and 2) providing a negative pressure support to the patient if the first characteristic is above a second target. When the positive pressure support is provided to the patient, the pressure provided to the patient during inspiration is higher than the pressure provided to the patient during expiration. When the negative pressure support is provided to the patient, the pressure provided to the patient during inspiration is lower than the pressure provided to the patient during expiration.

Another aspect provides a system for ventilating a patient. The system includes means for delivering a flow of gas to the airway of a patient from a source of breathing gas via a patient circuit, measuring a characteristic associated with the flow of gas (such as flow rate), and determining a first characteristic based on the measured characteristic. The system also includes means for controlling delivery of the flow of gas to the patient by 1) providing positive pressure support to the patient if the first characteristic is below a first target and 2) providing a negative pressure support to the patient if the first characteristic is above a negative target.

When the positive pressure support is provided to the patient, the pressure provided to the patient during inspiration is higher than the pressure provided to the patient during expiration. When the negative pressure support is provided to the patient, the pressure provided to the patient during inspiration is lower than the pressure provided to the patient during expiration.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. In one embodiment of the invention, the structural components illustrated herein can be considered drawn to scale. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

FIG. 1 illustrates a typical Cheyne-Stokes respiratory cycle that is treated by the pressure support system of the present invention;

FIGS. 2A and 2B illustrate waveforms of the patient flow and waveforms of the pressure being delivered to the patient, respectively, in accordance with an embodiment;

DETAILED DESCRIPTION OF EXEMPLARY EMBODIMENTS

FIG. 2A illustrates flow waveform, i.e., a graph of the measure rate of flow of gas at the airway of the patient, and FIG. 2B illustrates waveform of pressure support delivered to the patient by a pressure support system 10 (sec FIG. 3) in accordance with an embodiment. System 10 uses these patient flow values to obtain other measures of patient flow, such as, for example, peak flow, tidal volume, average inspiratory flow, minute ventilation, or other measures. Initially, as indicated by arrow C in FIG. 2B, the patient experiences a CSR event. During the hyperneic phase of the CSR pattern, negative pressure support is enabled and delivered to the patient, as indicated by arrow D. Positive pressure support and negative pressure support may be applied until the CSR events have been reduced or eliminated. Positive pressure support as used herein is where the IPAP level is higher than the EPAP level. In contrast, the negative pressure support as used herein is where the IPAP level is lower than the EPAP level. Negative pressure support may be provided when both the inspiratory and expiratory pressures are above atmospheric pressure, or when either pressure is at or below atmospheric pressure. Thus, to provide negative pressure support, the IPAP level may be decreased or the EPAP level may be increased so that IPAP level is lower than the EPAP level. Negative pressure support may be undesirable, uncomfortable and unnecessary when the patient is awake or aroused from sleep. Therefore, in some embodiments, the system 10 monitors for the waxing-waning pattern of CSR to ensure that CSR is occurring before enabling negative pressure support.

Figure 3:
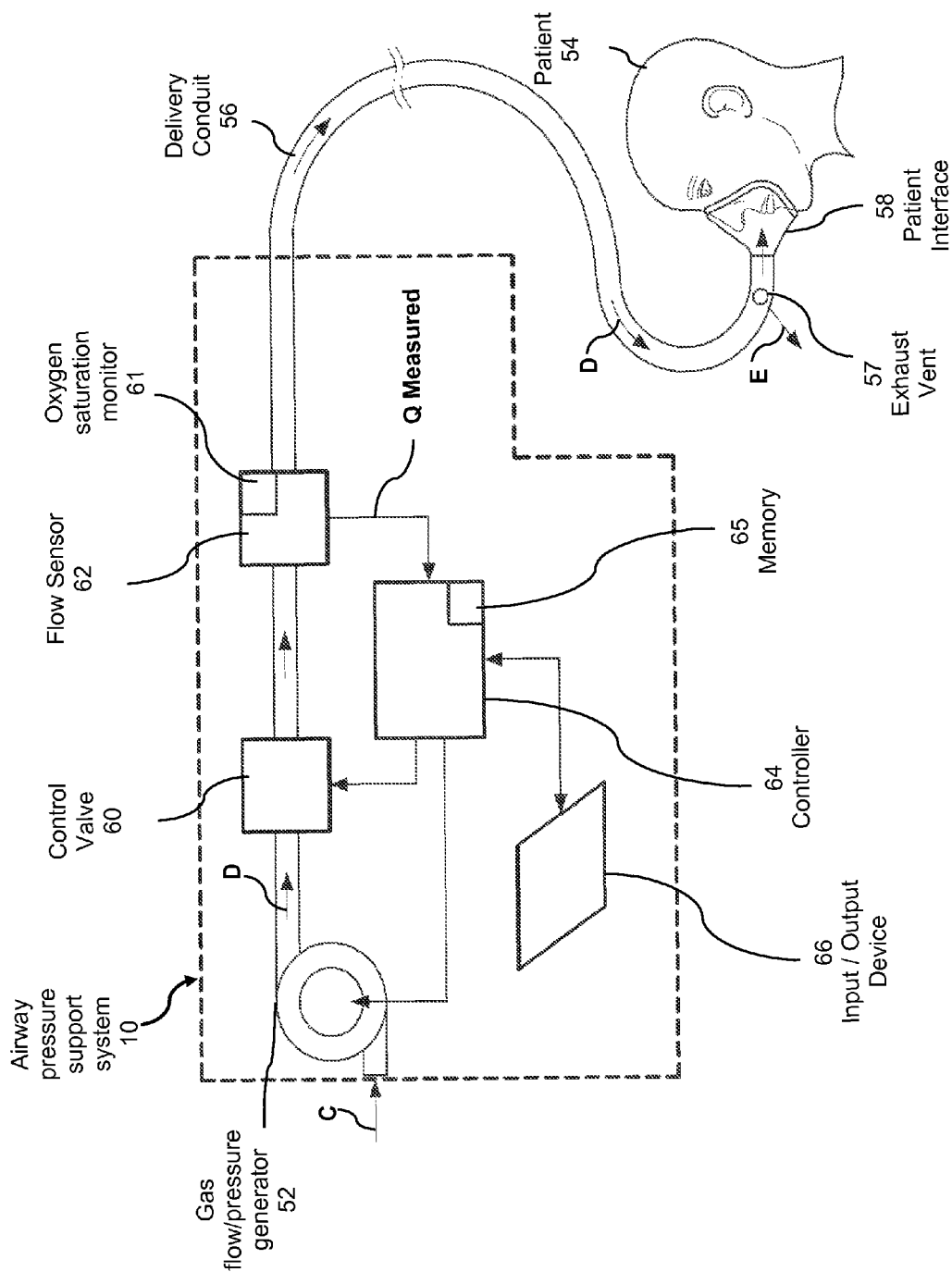
FIG. 3 is a functional block diagram of a positive airway pressure support system adapted to implement the pressure support therapy according to the principles of the present invention.

FIG. 3 schematically illustrates an airway pressure support system 10 suitable for providing an improved variable positive airway pressure mode of pressure support to a patient according to the principles of the present invention. This mode of pressure support is particularly suited to treat Cheyne-Stokes respiration. Pressure support system 10 includes a gas flow/pressure generator 52, such as a blower used in a conventional CPAP or bi-level pressure support device, piston, bellows, compressor, or any other device that receives breathing gas, generally indicated by arrow C, from any suitable source, e.g., a pressurized tank of oxygen or air, the ambient atmosphere, or a combination thereof. Gas flow/pressure generator 52 generates a flow of breathing gas, such as air, oxygen, or a mixture thereof, for delivery to an airway of a patient 54 at relatively higher and lower pressures. System 10 may also include devices or components to provide breathing gas at a pressure that is below atmospheric. That is, in some embodiments, system 10 may include two blowers and a valve configured to provide breathing gas at a pressure that is below atmospheric.

The pressurized flow of breathing gas, generally indicated by arrow D from gas flow/pressure generator 52 is delivered, via a delivery conduit 56, to a breathing mask or patient interface 58 of any known construction, which is typically worn by or otherwise attached to a patient 54 to communicate the flow of breathing gas to the airway of the patient. Delivery conduit 56 and patient interface device 58 are typically collectively referred to as a patient circuit.

In one embodiment, the variable positive airway pressure support system essentially functions as a bi-level pressure support system, and, therefore, includes all of the capabilities necessary in such systems in order to provide separate IPAP and EPAP levels to the patient. This includes receiving the necessary parameters via input commands, signals, instructions or information for providing a bi-level pressure, such as maximum and minimum IPAP and EPAP settings. The flow signal $Q_{measured}$ from a flow sensor 62 is also provided to the pressure support process, which controls the pressure controller to output the desired inspiratory and expiratory waveforms. Typically, carrying out the pressure support operation includes estimating or determining the actual patient flow $Q_{patient}$ based on the flow signal $Q_{measured}$, determining whether the patient is in the inspiratory or expiratory phase of the respiratory cycle and providing an I/E state signal indicative of the respiratory state of the patient, and triggering and cycling the pressure support system 10.

Pressure support system 10 shown in FIG. 3 is a single-limb system, meaning that the patient circuit includes only a delivery conduit 56 connecting the patient to the pressure support device. As such, an exhaust vent 57 is provided in the delivery conduit for venting exhaled gases from the system as indicated by arrow E. It should be noted that the exhaust vent can be provided at other locations in addition to or instead of in the delivery conduit, such as in the patient interface device. It should also be understood that the exhaust vent can have a wide variety of configurations depending on the desired manner in which gas is to be vented from pressure support system 10.

Pressure support system 10 may optionally be a two-limb system, having a delivery conduit and an exhaust conduit connected to the patient.

In the illustrated embodiment of the present invention, patient interface 58 is a nasal/oral mask. It is to be understood, however, that patient interface 58 can include a nasal mask, nasal pillows, tracheal tube, endotracheal tube, or any other device that provides the gas flow communicating function. Also, as used herein, the phrase "patient interface" can include delivery conduit 56 and any other structures that connect the source of pressurized breathing gas to the patient.

It is to be understood that various components may be provided in or coupled to the patient circuit. For example, a bacteria filter, pressure control valve, flow control valve, sensor, meter, pressure filter, humidifier and/or heater can be provided in or attached to the patient circuit. Likewise, other components, such as muffler and filters can be provided at the inlet of gas flow/pressure generator 52 and at the outlet of valve 60.

In the illustrated embodiment, variable positive airway pressure support system 10 includes a pressure controller. In one embodiment, the pressure controller can take the form of a control valve 60 provided in delivery conduit 56. Valve 60 controls the pressure of the flow of breathing gas from gas flow/pressure generator 52 delivered to the patient. For present purposes, gas flow/pressure generator 52 and valve 60 are collectively referred to as a "pressure generating system" because they act in concert to control the pressure and/or flow of gas delivered to the patient.

It should be apparent that other techniques for controlling the pressure delivered to the patient by the gas flow/pressure generator, such as varying the blower speed, either alone or in combination with a pressure control valve may be used. Thus, valve 60 is optional depending on the technique used to control the pressure of the flow of breathing gas delivered to the patient. If valve 60 is eliminated, the pressure generating system may correspond to gas flow/pressure generator 52 alone, and the pressure of gas in the patient circuit is controlled, for example, by controlling the motor speed of the gas flow/pressure generator.

Pressure support system 10 further includes a sensor 62 that measures a characteristic associated with the flow of gas within delivery conduit 56. In an exemplary embodiment, sensor 62 is a flow sensor that measures a rate of flow of gas within the delivery conduit. Sensor 62 can be any conventional flow sensor, such a pressure drop based flow sensor, ultrasonic flow sensor, or any other sensor capable of monitoring or measuring the rate of flow of gas within delivery conduit. In accordance with an embodiment shown in FIG. 2, flow sensor 62 is interposed in line with delivery conduit 56, such as downstream of valve 60. Flow sensor 62 generates a flow signal $Q_{measured}$ that is provided to a controller 64 and is used by the controller to determine the flow of gas at the patient $Q_{patient}$.

Techniques for calculating $Q_{patient}$ based on $Q_{measured}$ are well known, and take into consideration the pressure drop of the patient circuit, known leaks from the system, i.e., the intentional exhausting of gas from the circuit as indicated by arrow E in FIG. 2, and unknown leaks from the system, such a leaks at the mask/patient interface. Any conventional technique for calculating leak flow may be used, and this calculation may be used in calculating $Q_{patient}$ based on $Q_{measured}$. Examples of such techniques are taught by U.S. Pat. Nos. 5,148,802; 5,313,937; 5,433,193; 5,632,269; 5,803,065; 6,029,664; 6,539,940; 6,626,175, and 7,011,091, the contents of each of which are incorporated by reference into the present invention.

Other techniques for measuring the patient flow of the patient may be used. For example, the flow can be measured directly at the patient, in which case the measured flow corresponds directly the patient flow $Q_{patient}$ and no flow estimation is necessary. It is also contemplated that flow may be measured at other locations along delivery conduit 56.

In addition, the estimated patient flow $Q_{patient}$ may be determined based on other characteristics of the pressure support system 10. For example, the operation of the gas flow/pressure generator or a flow/pressure controller, such as a valve, is affected by the flow in the patient circuit, or by the systems attempt to maintain the pressure in the system. As a result, monitoring a characteristic of the system, such as monitoring the power, torque, and/or rotating speed of the pressure generator or the position of the valve, can be used as a surrogate for measuring the patient flow directly. It is also known to measure patient flow using a flow sensor upstream of the gas flow/pressure generator. Any combination of such flow measuring techniques can also be used. In these latter cases, an estimation of patient flow $Q_{patient}$ based on the measured flow or other parameter will be needed.

An input/output device 66 is provided for setting various parameters used by the variable positive airway pressure support system 10, as well as for displaying and outputting information and data to a user, such as a clinician or caregiver. Input/output terminals may optionally be provided so that the operation information and data collected by the pressure support system 10 can be monitored and controlled remotely. Controller 64 may be or include a microprocessor that is/are capable of implementing and executing routines for monitoring characteristics of patient respiration and controlling the flow of breathing gas based thereon as discussed in detail below. In addition, in one embodiment, controller 64 includes memory, or memory arrays 65 for storing and buffering information necessary to implement the techniques discussed herein. It is to be understood, that controller 64 can be a single processing component, or can be comprised of multiple components (memories, processor, arrays, logic circuits, etc.) operating in conjunction to implement the techniques discussed herein.

In an embodiment, controller 64 controls gas flow/pressure generator 52, valve 60, or both to deliver a pressure waveform to an airway of patient 54. In an embodiment, the pressure waveform is essentially a bi-level pressure waveform that alternates between an IPAP level and an EPAP level (see FIGS. 4A and 4B). In some embodiments, the IPAP level is variable under the direction of controller 64 as discussed below. The maximum and minimum IPAP levels ($IPAP_{max}$, $IPAP_{min}$) are provided to the controller via input device 66 from a user. Alternatively or additionally, the EPAP level is variable under the direction of controller 64 (see FIGS. 4A and 4B). In such embodiments, the maximum and minimum IPAP levels ($EPAP_{max}$, $EPAP_{min}$) are provided to the controller via input device 66 from a user. It should be understood that the maximum and minimum IPAP/EPAP levels can also be pre-established and stored in the controller as a default or in lieu of input parameters from the system operator.

Figure 4A:
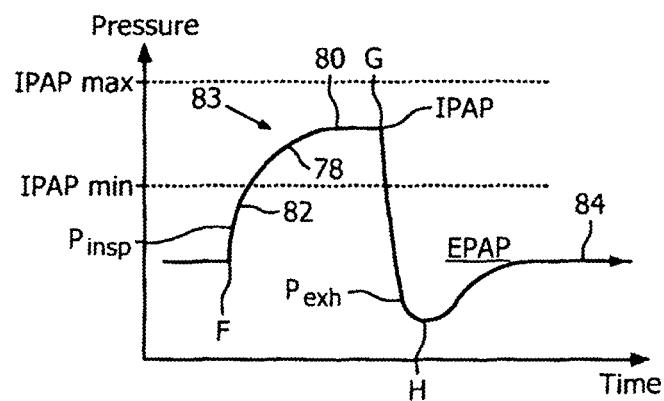
FIGS. 4A-4B illustrate exemplary pressure waveforms delivered by the pressure support system of FIG. 3 in accordance with an embodiment.
Figure 4B:
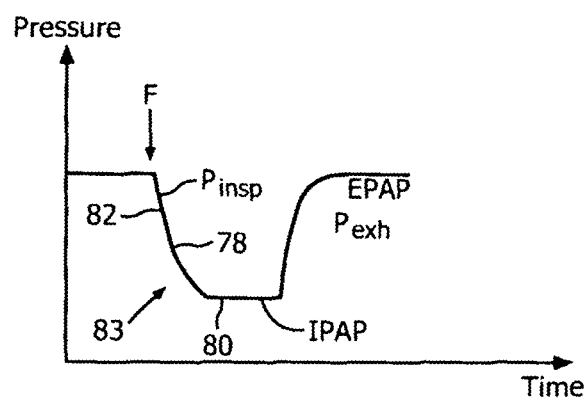

FIGS. 4A and 4B illustrates exemplary pressure waveform 78 that can be provided by the pressure support system 10 to treat CSR. As shown in FIGS. 4A and 4B, at time F, which is the trigger point from expiration to inspiration, the patient begins inspiring and triggers the pressure support system 10 to transition to an IPAP level 80. The shape and duration of the pressure increase or rise 82 from trigger point F to the IPAP level can be fixed or variable, as taught for example, in U.S. Pat. Nos. 5,598,838; 5,927,274; 6,532,960; and 6,640,806, the contents of each of which are incorporated herein by reference. In the illustrated embodiment, the shape of the pressure increase is exponential. It is to be understood that other shapes, such as step functions or linear ramps are contemplated for the pressure rise portion of an inspiratory portion 83 of the pressure waveform.

It should be further understood that the present invention contemplates that an inspiratory portion 83 and the expiratory portion $P_{exh}$ of pressure waveform 78 can have a variety of configurations. That is, the pressure waveform during inspiration $P_{insp}$ and/or the expiratory portion $P_{exh}$ can be controlled using conventional pressure support or ventilation techniques, such as proportional assist ventilation (PAV®), which is described in U.S. Pat. Nos. 5,044,362 and 5,107,830, or proportional positive airway pressure (PPAP), which is described in U.S. Pat. Nos. 5,535,738; 5,794,615; 6,105,575; and 6,609,517 ("the PPAP patents") the contents of each of which are incorporated herein by reference. According to the PPAP patents, the waveform for inspiratory pressure, $P_{insp}$, output by pressure support system 10 during the inspiratory phase of the breathing cycle may be determined according to the following equation:

$$P_{insp} = IPAP + Gain_{insp} * Q_{patient} \qquad \text{Eq. 1.1}$$

where $Gain_{ins}$ is a gain factor, typically selected by a caregiver. $Gain_{ins}$ can be set to any value including a value of one (1).

The expiratory pressure, $P_{exh}$, output by pressure support system 10 during the expiratory phase of the breathing cycle may be determined according to the following equation:

$$P_{exh} = EPAP + Gain_{exh} * Q_{patient}, \qquad \text{Eq. 1.2}$$

where $Gain_{exh}$ is a gain factor, typically selected by a caregiver. $Gain_{exh}$ can be set to any value including a value of one (1).

It should be noted that for present purposes, flow into the patient is considered positive flow, and flow out of the patient is considered negative flow. Thus, the value of the patient flow $Q_{patient}$ is taken at the patient's airway. The flow measured at a location distal from the patient $Q_{measured}$ may have a positive offset due, for example, to exhausting of gas from the circuit, which is factored out by leak estimation techniques.

Controller 64 receives flow $Q_{measured}$ from flow sensor 62 and implements equations 1.1, 1.2, or both, for generating the inspiratory pressure waveform $P_{insp}$ and expiratory pressure waveform $P_{exh}$.

Figure 5:
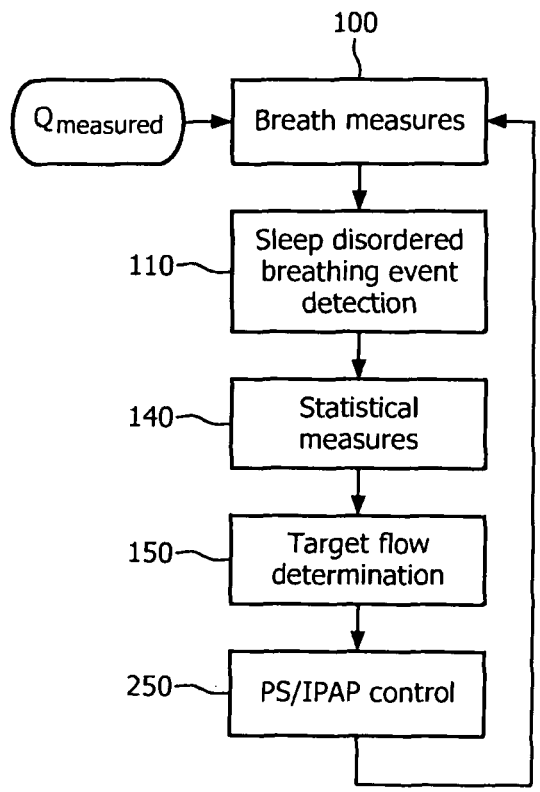
FIG. 5 is a flowchart illustrating a portion of the process for implementing the pressure support mode of the present invention.

Controller 64 implements an algorithm to control the pressure of the flow of gas delivered to the patient. The process shown in FIG. 5 shows the algorithm performed by the pressure support system 10 during each breath. As shown in FIG. 5, a primary input to this algorithm is the output of flow sensor 62 ($Q_{measured}$). The output is sampled at a sampling rate, such as 100 samples/second, to produce a new estimated patient flow $Q_{patient}$ determination every 10 milliseconds. $Q_{patient}$ may be calculated based on $Q_{measured}$ using known flow/leak estimation techniques. $Q_{patient}$ can also be measured directly at the mask so that flow estimation is not needed. The measured flow $Q_{measured}$ may optionally be used directly for the calculations of the present invention, recognizing that the measured flow is not an accurate representation of the flow at the airway of the patient.

A history of the patient flow $Q_{patient}$ or a measure of the patient flow is stored in memory to perform the flow analysis discussed below. Controller 64 includes storage arrays and buffers to calculate parameters in real-time, and store the results in moving windows.

According to one aspect of the present invention, controller 64 monitors the patient flow to determine the transitions from inspiration to expiration and from expiration to inspiration. Any suitable techniques may be used, such as using both volume and wave shape to (a) trigger the device to provide the inspiratory pressure $P_{insp}$ and (b) cycle the device to provide the expiratory pressure $P_{exh}$, which are described in U.S. Pat. Nos. 5,148,802; 5,313,937; 5,433,193; 5,632,269; 6,029,664; 6,539,940; and 6,626,175.

FIG. 5 is a flow chart illustrating a portion of the process for implementing the pressure support mode of the present invention. In step 100, in some embodiments, the controller analyzes the patient's instantaneous flow $Q_{patient}$ to produce measures of flow (i.e., a first characteristic of the measured characteristic, which can be flow). In one embodiment, $Q_{patient}$ is used to calculate the instantaneous average inspiratory flow ($Q_{ave}(t)$) and maximum instantaneous average inspiratory flow ($Q_{ave}(max)$), which are continuously calculated during the inspiratory phase of the respiratory cycle. The instantaneous average inspiratory flow is the summation of positive, i.e., inspiratory, patient flows over a period of time divided by the number of samples taken during that period of time. The Maximum Average Inspiratory Flow ($Q_{ave}(max)$) is the maximum value of the Instantaneous Average Inspiratory Flow over one breath, i.e., during the inspiratory phase of the respiratory cycle. It can thus be appreciated that during one given inspiratory phase of a patient's respiratory cycle, a continuum of $Q_{ave}(t)$ is calculated over the entire inspiratory phase, and only one $Q_{ave}(max)$ is found. In another embodiment, $Q_{patient}$ is used to calculate the Tidal Volume, Minute Ventilation, or any other measures of flow.

As mentioned above, Cheyne-Stokes respiration (CSR) pattern 30 is characterized by rhythmic waxing periods 32 and waning periods 34 of respiration, with regularly recurring periods of high respiratory drive (hyperpnea) 36 and low respiratory drive (hypopnea or apnea) 38. The present invention monitors for CSR to ensure that the pressure therapy being applied to the patient is sufficient to treat CSR. Naturally, the presence of CSR indicates that the therapy is not effective. Thus, it is important that CSR events be detected accurately and monitored. The steps to detect CSR may be implemented in software run by the processor in the pressure support system 10. The present invention contemplates and those skilled in the art would appreciate that any suitable CSR detection technique can be used to monitor the effectiveness in the CSR treatment delivered to the patient. For example, CSR may be detected by monitoring the measure of flow and using the CSR Index and Flow Ratio values, as described in U.S. patent application Ser. No. 11/235,520, which is incorporated herein in its entirety. CSR may also be detected by monitoring the oxygen saturation of the user, which may be monitored using a pulse oximeter 61 (shown in FIG. 3). An increase in the oxygen saturation may coincide with the waxing period of the CSR pattern, and a decrease in the oxygen saturation level may coincide with the waning period at the end of the CSR cycle. Thus, the oxygen saturation level may be monitored to identify the ascending and descending states that indicate that the patient has experienced a CSR cycle.

In some embodiments, CSR may also be detected by comparing the peak flow for the current breath ($Q_{peak}(k)$) with the peak flow for the immediately preceding breath cycle ($Q_{peak}(k-1)$) to determine the presence of CSR, as described in U.S. Pat. No. 7,267,122, which is incorporated herein in its entirety. In such embodiments, the system 10 may look for patterns comprising upward trends (crescendos), peak flow peaks (hyperpnea), downward trends (decrescendo), and peak flow valleys (hypopnea or apnea).

Any conventional technique may be used for detecting apneas and hypopneas. In its most basic form, apnea and hypopnea detection involves monitoring the patient flow $Q_{patient}$ for reductions in flow below a threshold level for a predetermined period of time. The threshold level and predetermined periods of time are levels deemed to constitute an apnea or hypopnea, i.e., meet the definition of an apnea or hypopnea.

In one embodiment, as shown in FIG. 5, the apnea and hypopnea detection techniques taught by published U.S. patent application. Ser. No. 10/268,406 (publication no US-2003-0111079-A1) ("the '079 application") are used in step 110. The contents of the '079 application are incorporated herein by reference. In some embodiments, the weighted peak flow $Q_{wpeak}$ or the peak to peak flow of the previous breath may be used during apnea and hypopnea detection.

Periodic breathing events may also be detected using any conventional techniques. In embodiments where the maximum average inspiratory flow $Q_{ave}(max)$ is used as the measure of flow, a periodic breathing event is declared if a patient is deemed to have too much irregularity in the $Q_{ave}(max)$. Such method for detecting a periodic breathing event is described in U.S. patent application Ser. No. 11/235,520, which is incorporated herein in its entirety.

Figure 6:
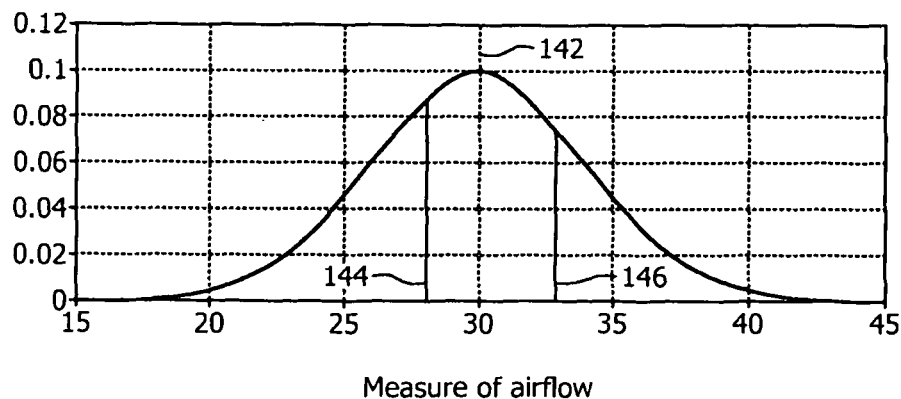
FIG. 6 is an example of a normal distribution curve for an array of Maximum Average Inspiratory Flows.

Referring back to FIG. 5, the algorithm uses statistical functions in step 140 to determine a level of ventilation which has been demonstrated by the patient over the last several minutes of breathing. The following statistical measures or characteristics based on the measure of flow may be calculated by controller 64 in step 140:
1) Mean,
2) 60th percentile,
3) 95% of mean,
4) Standard Deviation, and
5) Standard Mean For example, in an embodiment that uses $Q_{ave}(max)$ as the measure of flow, FIG. 6 illustrates an exemplary normal distribution of values for $Q_{ave}(max)$ around a mean 142 having a value of 30 with a standard deviation of 4. In this example, 95% of the mean is 28.5 lpm and is indicated by line 144. The 60th percentile of the data is 33.2 lpm and is indicated by line 146. Standard Mean is the ratio of Standard Deviation over the mean expressed as a percentage. Other measures or characteristic may optionally be used instead of the $Q_{ave}(max)$ value, such as the mean flow, peak flow, tidal volume, minute ventilation, or other measures.

Referring back to FIG. 5, the algorithm in step 150 determines a Target value that is used in determining the pressure support to be delivered to the patient by the pressure support system 10. The Target is a value against which a first characteristic, such as the current measure of flow, is compared to determine whether the pressure support needs to be changed or delivered. There may optionally be a single target, dual targets, or multiple targets.

Figure 7:
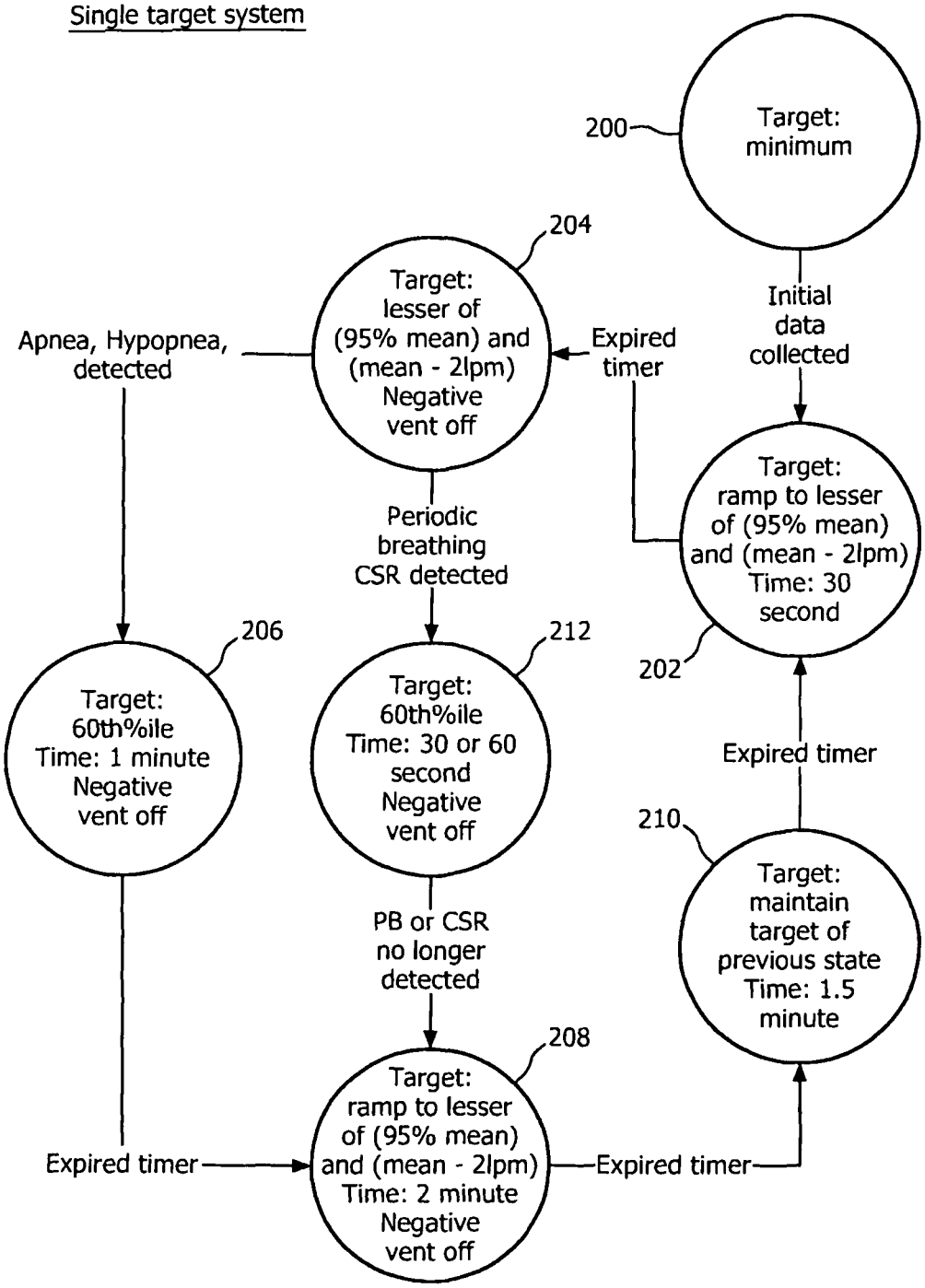
FIG. 7 is a state diagram explaining the single Target selection process in accordance with an embodiment.

FIG. 7 is a state diagram showing, in detail, the process for selecting the statistical measure to be used as the Target. When the pressure support system 10 is actuated, the Target selection process starts at step 200, where the Target is set to a minimum value and initial data is collected. Because a single Target is used in this embodiment for negative pressure support and positive pressure support, the single Target can be considered both the Negative Target and the Positive Target. In an embodiment, the minimum value for the Target is determined empirically. In the present embodiment, this minimum Target is set to 15 lpm. It is to be understood, however, that the present invention contemplates that the Target can be set by the system based on monitored physiological characteristics of the patient, such as whether the patient is deemed to be experiencing sleep disordered breathing, flow limitations, etc.

In step 202, the Target is increased to (1) a value that corresponds to 95% of the mean value of the measure of flow data thus collected or to (2) a value that corresponds to the mean value of the measure of flow minus a fixed flow rate, which ever is smaller. In an embodiment, this fixed flow rate is 2 lpm. In an embodiment, the increase in the Target is done in a linear, ramp fashion over a period of time that spans several respiratory cycles, such as 30 seconds. This ramp in the Target is done to avoid rapid pressure fluctuations being introduced to the patient, thereby optimizing patient comfort and compliance with the treatment. The shape or pattern for the change (ramp) in the Target can be done at a fixed rate, so that the ramp is linear. It can also be done at non-linear rates, so that the ramp shape is not linear. In an embodiment, ramp in Target takes place at a rate of 0.5 lpm per breath.

In step 204, the Target value is maintained at (1) a value that corresponds to 95% of the mean value of the measure of flow or at (2) a value that corresponds to the mean value of measure of flow minus a fixed flow rate, which ever is smaller. In an embodiment, this fixed flow rate is 2 lpm, so that the Target is maintained at 95% of measure of flow or at the mean value of (measure of flow-2 lpm), whichever is smaller. In this step, the negative ventilation is disabled. If, however, a sleep disordered breathing event, such as an apnea or hypopnea, is detected the process moves to step 206, where the Target is changed to the 60th percentile. This increase in the Target provides a greater likelihood that the system will increase the pressure support, and, thus treat the sleep disordered breathing event, than if the Target is not changed. At this step, the negative pressure support is still disabled. The Target is maintained at this level for a period of time, such as one minute. After that, the process moves to step 208.

In step 208, the Target is changed back to the lesser of 1) 95% of the mean value of the measure of flow data currently collected or 2) the mean value of measure of flow minus a fixed flow rate, such as 2 lpm. In an embodiment, this change takes place in a linear, ramp fashion, over a period of time that spans several respiratory cycles, such as 2 minutes at a rate of 0.5 lpm per breath. The change in Target can also be done at a non-linear rate.

The system maintains the Target at its current value in a hold state in step 210. This is done to allow the patient to stabilize under the new value for the Target. This prevents the system of the present invention from overcompensating or being too aggressive in its reactions to the monitored condition of the patient. In an embodiment, this hold state lasts for 1.5 minutes. Other periods of time may optionally be used, and this period of time can be selected dynamically by the system. After the 1.5 minute hold, the process returns to step 202.

If a CSR event or periodic breathing is detected during step 204, the process moves to step 212, where the Target is changed to the 60th percentile. In this step, negative pressure support is enabled. As used herein, "enabled" means that the system is able to deliver negative pressure support to the patient and does not mean that negative pressure support must be delivered to the patient. That is, it is possible for the system to deliver negative pressure support to the patient. In addition, as used herein, "deliver" or "delivered" means actually providing negative pressure support to the patient. At this step 204, if the measure of flow exceeds the negative target, then negative pressure support is delivered to the patient. The Target is maintained at this level for a relatively short period of time, such as 30 seconds. If no CSR events are detected during this 30 second window, the process moves to step 208. If CSR is still detected, the timer is reset. The process proceeds to step 208 when periodic breathing or CSR is no longer detected and the 30 seconds has elapsed.

Figure 8:
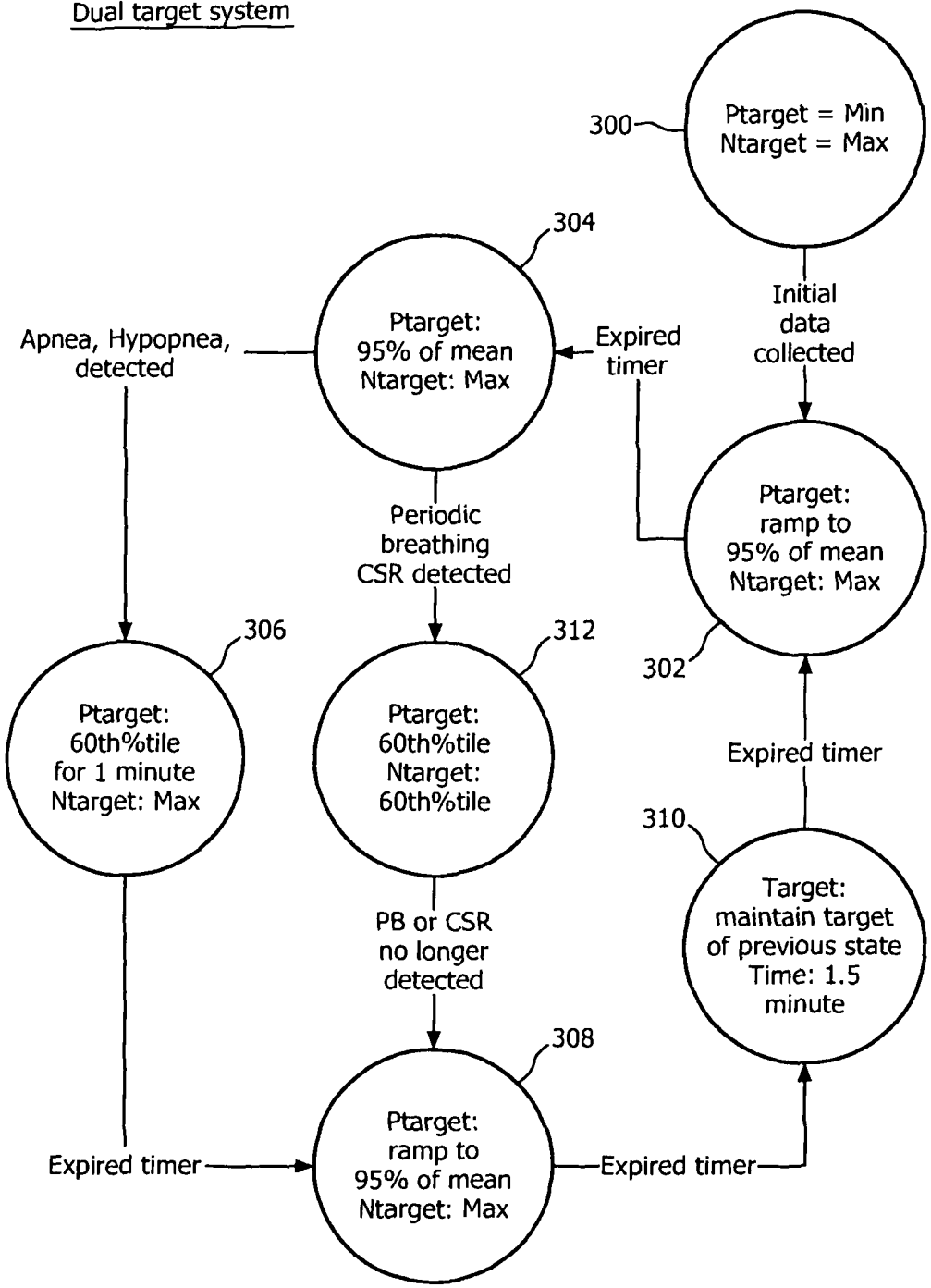
FIG. 8 is a state diagram explaining the dual Target selection process in accordance with an embodiment.

FIG. 8 is a state diagram showing, in detail, the process for selecting the statistical measures to be used as the dual Targets (the Negative Target and the Positive Target). When the pressure support system 10 is actuated, the Negative and Positive Target selection process starts at step 300, where the Positive Target is set to a minimum value, the Negative Target is set to a maximum value, and initial data is collected. In an embodiment, the minimum and maximum values for the Negative Target and the Positive Target are determined empirically. In some embodiments, this minimum Target is set to 15 lpm. In some embodiments, the maximum Target is set to 50 lpm. It is to be understood, however, that the present invention contemplates that the Negative Target and Positive Target can be set by the system based on monitored physiological characteristics of the patient, such as whether the patient is deemed to be experiencing sleep disordered breathing, flow limitations, etc.

In step 302, the Positive Target is increased to a value that corresponds to 95% of the mean value of the measure of flow data thus collected. In an embodiment, the increase in the Target is done in a linear, ramp fashion over a period of time that spans several respiratory cycles, such as 30 seconds. This ramp in the Target is done to avoid rapid pressure fluctuations being introduced to the patient, thereby optimizing patient comfort and compliance with the treatment. The shape or pattern for the change (ramp) in the Target can be done at a fixed rate, so that the ramp is linear. It can also be done at non-linear rates, so that the ramp shape is not linear. In an embodiment, ramp in Target takes place at a rate of 0.5 lpm per breath. The Negative Target is maintained at the maximum value. In some embodiments, this setting for the Negative Target essentially disables negative target support. As mentioned above, negative pressure support is delivered to the patient when the measure of flow exceeds the Target. In embodiments having dual Targets, negative pressure support is delivered to the patient when the measure of flow exceeds the Negative Target. As such, if the Negative Target is set to a high value, the measure of flow might not be able to exceed the Negative Target criteria for the negative pressure support to be delivered.

In step 304, the Positive Target value is maintained at the value that corresponds to 95% of the mean value of the measure of flow. The Negative Target is maintained at the maximum value.

If, however, a sleep disordered breathing event, such as an apnea or hypopnea, is detected the process moves to step 306, where the Target is changed to the 60th percentile. This increase in the Target provides a greater likelihood that the system will increase the pressure support, and, thus treat the sleep disordered breathing event, than if the Target is not changed. At this step, the Negative Target is still maintained at the maximum level. As mentioned above, in some embodiments, this setting for the Negative Target essentially disables negative pressure support. The Positive Target and the Negative Target are maintained at this level for a period of time, such as one minute. After that, the process moves to step 308.

In step 308, the Positive Target is changed back to the 95% of the mean value of the measure of flow data currently collected. In an embodiment, this change takes place in a linear, ramp fashion, over a period of time that spans several respiratory cycles, such as 2 minutes at a rate of 0.5 lpm per breath. The change in Positive Target can also be done at a non-linear rate. The Negative Target is maintained at the maximum value.

The system maintains the Positive Target and the Negative Target at its current value in a hold state in step 310. As mentioned above, this is done to allow the patient to stabilize under the new value for the Positive and Negative Targets. This prevents the system of the present invention from overcompensating or being too aggressive in its reactions to the monitored condition of the patient. In an embodiment, this hold state lasts for 1.5 minutes. Other periods of time may optionally be used, and this period of time can be selected dynamically by the system. After the 1.5 minute hold, the process returns to step 302.

If a CSR event or periodic breathing is detected during step 304, the process moves to step 312, where the Positive Target is changed to the 60th percentile. The Negative Target is changed to the 65 percentile. At this step 312, if the measure of flow exceeds the Negative Target, then negative pressure support is delivered to the patient. The Positive and Negative Targets are maintained at this level for a relatively short period of time, such as 30 seconds. If no CSR events are detected during this 30 second window, the process moves to step 308. If, however, CSR events continue to be detected, the system will continue to hold the timer in reset and the process will remain in step 312. The process proceeds to step 308 when periodic breathing or CSR is no longer detected and the 30 seconds has elapsed.

It can be appreciated that the negative pressure support may be enabled during other steps, instead of or in addition to when CSR has been detected. For example, negative pressure support may be enabled throughout the entire treatment and may be delivered when the measure of flow exceeds the negative target. In some embodiments, negative pressure support may be enabled when repetitive apneas or hypopneas are identified.

The negative pressure support may also be enabled only during certain phases. For example, in some embodiments, negative pressitre support is enabled only during the hyperpneic phase of either CSR or repetitive apncas/hypopneas. In such embodiments, system 10 may monitor the measure of flow to determine when the patient has entered a hyperpneic phase. Once the patient has been determined to be in the hyperpneic phase, the negative pressure support is enabled. As mentioned above, negative pressure support may be delivered when the measure of flow is above a target.

It is also contemplated that the negative pressure support may be disabled after a predetermined period of time or after the occurrence of an event. For example, negative pressure support may be disabled after the apneas or hypopneas have stopped occurring, or if arousal from sleep is detected.

It can be appreciated that the embodiments are not to be limited to the specific time periods, percentages, and constants noted above. Rather, other values for these quantities can be used so long as the general principles of the present invention are maintained. In addition, these quantities need not be fixed. Instead, they can be dynamically altered by the controller based on the monitored condition of the patient. This can be done, for example, to treat the patient more aggressively if they are not responding to the current treatment scheme, and vise versa.

Controller 64 determines the amount of pressure that must be provided to the patient to eliminate or reduce CSR. As noted above, in some embodiments, either one or both of IPAP and EPAP levels may be varied by the controller. In some embodiments, one of IPAP or EPAP may be manually set or pre-established, and the other of the IPAP or EPAP levels may be varied by the controller 64.

Referring back to FIG. 5, in some embodiments, the IPAP/EPAP pressure to be delivered to the patient in step 250 may be determined based on 1) the current measure of flow, such as the $Q_{ave}(max)$ in some embodiments, 2) the pressure support delivered during the previous breath, 3) the Target value determined in step 150, and 4) a gain factor. As noted above, the pressure support is the difference between the TAT level and the EPAP level.

In some embodiments, the following algorithm may be used to determine the pressure support delivered to a patient during a current breath (k+1):

$$PS(k+1)=PS(k)+Gain*(Target-Q_{ave}(max)(k)) \quad \text{Eq. 1.3}$$

where k is the index of the last breath, PS(k) is the pressure support delivered during the previous breath, Gain is a factor that converts flow into pressure, Target is determined as discussed above, and $Q_{ave}(max)$ (k) is the Maximum Average Inspiratory Flow $Q_{ave}(max)$ from the previous breath. In some embodiments, the Gain factor may be a 30 breath average of a ratio of pressure support (PS) over the Maximum Average Inspiratory Flow, as described in U.S. patent application Ser. No. 11/235,520, which is incorporated herein in its entirety.

It is important to note that the use of $Q_{ave}(max)$ in Eq. 1.3 as the measure aye, of flow is not intended to be limiting. Other measures of flow may be used, just for example, tidal volume, minute ventilation, or mean flow. Thus, mean flow, tidal volume, or minute ventilation may be compared against a target mean flow, a target tidal volume, or a target minute ventilation.

The process shown in FIG. 5 shows the calculations that are performed by the pressure support system 10 during each breath. The controller 64 determines whether to provide positive pressure support or negative pressure support. That is, if the measure of flow is below the Target or the Positive Target, positive pressure support is provided, wherein the IPAP level is higher than the EPAP level. If the measure of flow is above the Target or the Negative Target, negative pressure support is provided, wherein the EPAP level is higher than the IPAP level. The pressure support system 10 may deliver pressure support using the methods described in U.S. patent application Ser. No. 11/235,520 and U.S. Pat. No. 7,267,122, which are incorporated herein in its entirety. The controller 64 may determine whether it is in the inspiratory phase of the respiratory cycle. This may be accomplished using any conventional technique for differentiating between inspiration and expiration. In an embodiment, a flag is set whenever the patient is in inspiration. A flag may also be set whenever the patient is in expiration.

In embodiments where a flag is set during inspiration, if the patient is in the inspiratory phase of the respiratory cycle, the controller 64 causes the gas flow/pressure generator to begin to deliver the inspiratory pressure $P_{insp}$ to the patient based on the pressure support calculated in step 250 of FIG. 5 (see Eq. 1.3). In some embodiments, the controller 64 may cause the flow/pressure generator to begin to deliver the expiratory pressure to the patient based on the pressure support when the patient is in the expiratory phase of the respiratory cycle. Controller 64 may then control the pressure delivered to the patient during or within the respiratory cycle. The controller determines whether the pressure support delivered to the patient is sufficient. In some embodiments, the positive pressure support delivered thus far is considered to be sufficient if the positive pressure support delivered by the system during the inspiratory phase under the current magnitude and rate of increase will result in $Q_{ave}(t)$ meeting or exceeding the Target or the Positive Target. In some embodiments, the negative pressure support delivered thus far is considered to be sufficient if the negative pressure support delivered by the system under the current magnitude and rate of decrease will result in $Q_{ave}(t)$ meeting or being slightly below the Target or the Negative Target. In some embodiments, the controller 64 may deliver pressure support and determine if the pressure support delivered is sufficient, as described in U.S. patent application Ser. No. 11/235,520, and/or U.S. Pat. No. 7,267,122, which are hereby incorporated by reference in its entirety.

Controller 64 may implement any of the standard functions of a pressure support device, i.e., providing CPAP, bi-level pressure support BiPAP, PPAP pressure support, smart-CPAP as taught, for example, in U.S. Pat. Nos. 5,203,343; 5,458,137; and 6,087,747, the contents of which are incorporated herein by reference, or auto-titration CPAP as taught, for example, in U.S. Pat. No. 5,645,053, the contents of which are also incorporated herein by reference, in addition to implementing the CSR treatment mode of pressure support as disclosed herein. In one embodiment, the pressure support system 10 includes a mode select input device that allows a user or authorized caregiver to select the mode of ventilation (CSR treatment technique, CPAP, bi-level, auto-titration CPAP, PAV, PPAP, etc.) under which the pressure support device operates. In addition, CSR detection techniques may be performed in the background while implementing a conventional mode of pressure support and then switching to the CSR treatment mode of pressure support once CSR is detected.

Although the invention has been described in detail for the purpose of illustration based on what is currently considered to be the most practical embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is contemplated that, to the extent possible, one or more features of any embodiment can be combined with one or more features of any other embodiment.

What is claimed is:

1. A system for delivering a flow of gas to an airway of a patient, the system comprising:
   a gas flow generator configured to generate the flow of gas;
   a patient circuit coupled to the gas flow generator configured to communicate the flow of gas to the airway of the patient;

a sensor configured to generate output signals related to a characteristic associated with the flow of gas; and a controller configured to selectively control the flow of gas to the airway of the patient, wherein flow into the patient is positive flow and flow out of the patient is negative flow, from the gas flow generator via the patient circuit by operating in:

1) a first pressure mode responsive to the characteristic being below a first threshold, wherein the first pressure mode comprises providing the gas to the patient at a first inspiratory pressure during inspiration and a first expiratory pressure during expiration, and wherein the first inspiratory pressure is higher than the first expiratory pressure; and 2) a second pressure mode responsive to the characteristic being above a second threshold, wherein the second pressure mode comprises providing the gas to the patient at a second inspiratory pressure during inspiration and a second expiratory pressure during expiration, wherein the second expiratory pressure is higher than the second inspiratory pressure, and wherein the controller is configured such that the first inspiratory pressure is a first inspiratory positive airway pressure (IPAP) level and the first expiratory pressure is a first expiratory positive airway pressure (EPAP) level, and wherein the first IPAP level is higher than the first EPAP level in the first pressure mode; and wherein the second inspiratory pressure is a second IPAP level and the second expiratory pressure is a second EPAP level, and wherein the second EPAP level is higher than the second IPAP level in the second pressure mode; and whereby the first IPAP, first EPAP, second IPAP, and second EPAP are positive gas pressure in a flow direction towards the patient.

2. The system of claim 1, wherein the controller is configured to detect a predetermined breathing characteristic of the patient based on the characteristic associated with the flow of gas, and wherein the controller operates in the second pressure mode responsive to the predetermined breathing characteristic and the characteristic associated with the flow of gas being above the second threshold.

3. The system of claim 2, wherein the characteristic associated with the flow of gas is a sleep disorder breathing event.

4. The system of claim 3, wherein the controller alters the first threshold and the second threshold based on a determination that the patient is experiencing a sleep disordered breathing event.

5. The system of claim 3, wherein the sleep disorder breathing event is Cheyne-Stokes Respiration, hypopnea, or apnea.

6. The system of claim 1, wherein the characteristic associated with the flow of gas is Cheyne-Stokes Respiration, wherein the system further comprises an oxygen saturation monitor adapted to output a signal indicative of an oxygen saturation of the patient, and wherein the controller determines whether the patient is experiencing Cheyne-Stokes Respiration based, at least in part, on an output of the oxygen saturation monitor.

7. The system of claim 1, wherein the characteristic associated with the flow of gas is a flow rate.

8. The system of claim 1, wherein, responsive to the controller operating in the second pressure mode, the second expiratory pressure and the second inspiratory pressure are above atmospheric pressure.

9. The system of claim 1, wherein the first threshold is the same as the second threshold.

10. The system of claim 1, wherein the characteristic associated with the flow of gas is a Maximum Average Inspiratory Flow (Qave(max)), wherein the controller compares the Qave(max) to the first threshold and the second threshold, and wherein the controller controls the system based on this comparison.

11. The system of claim 1, wherein the characteristic associated with the flow of gas is a tidal volume, wherein the controller compares the tidal volume to the first threshold and the second threshold, and wherein the controller controls the system based on this comparison.

12. The system of claim 1, wherein the characteristic associated with the flow of gas is a minute ventilation, wherein the controller compares the minute ventilation to the first threshold and the second threshold, and wherein the controller controls the system based this comparison.

13. A method of ventilating a patient with a gas delivery system, the gas delivery system comprising a patient circuit, a sensor, and a controller, the method comprising:

delivering a flow of gas to an airway of the patient from a source of breathing gas via the patient circuit;

generating, with the sensor, output signals related to a characteristic associated with the flow of gas; and selectively controlling, with the controller, delivery of the flow of gas to the patient, wherein flow into the patient is positive flow and flow out of the patient is negative flow, by:

1) providing the flow of gas according to a first pressure mode responsive to the characteristic being below a first threshold, wherein the first pressure mode comprises providing the gas to the patient at a first inspiratory pressure during inspiration and patient first expiratory pressure during expiration, and wherein the first inspiratory pressure is higher than the first expiratory pressure; and 2) providing the flow of gas according to a second pressure mode responsive to the characteristic being above a second threshold, wherein the second pressure mode comprises providing the gas to the patient at a second inspiratory pressure during inspiration and a second expiratory pressure during expiration, wherein the second expiratory pressure is higher than the second inspiratory pressure, and wherein the first inspiratory pressure is a first inspiratory positive airway pressure (IPAP) level and the first expiratory pressure is a first expiratory positive airway pressure (EPAP) level, and wherein the first IPAP level is higher than the first EPAP level in the first pressure mode; and wherein the second inspiratory pressure is a second IPAP level and the second expiratory pressure is a second EPAP level, and wherein the second EPAP level is higher than the second IPAP level in the second pressure mode; and whereby the first IPAP, first EPAP, second IPAP, and second EPAP are positive gas pressure in a flow direction towards the patient.

14. The method of claim 13, wherein controlling the delivery of the flow of gas to the patient comprises detecting a predetermined breathing characteristic of the patient based on the characteristic associated with the flow of gas, and providing the flow of gas according to the second pressure mode to the patient responsive to the predetermined breathing characteristic being detected and the characteristic associated with the flow of gas being above the second threshold.

15. The method of claim 14, wherein the predetermined breathing characteristic is a sleep disorder breathing event.

16. The method of claim 15, wherein controlling the delivery of the flow of gas to the patient comprises altering the first threshold and the second threshold based on a determination that the patient is experiencing a sleep disordered breathing event.

17. The method of claim 15, wherein the sleep disorder breathing event is Cheyne-Stokes Respiration, hypopnea, or apnea.

18. The method of claim 14, wherein the predetermined breathing characteristic is Cheyne-Stokes Respiration, the method further comprising monitoring an oxygen saturation, with an oxygen saturation monitor of the gas delivery system, of the patient and determining whether the patient is experiencing Cheyne-Stokes Respiration based, at least in part, on the monitored oxygen saturation.

19. The method of aim 13, wherein responsive to providing the flow of gas according to the second pressure mode, both the second expiratory pressure and the second inspiratory pressure are above atmospheric pressure.

20. The method of claim 13, wherein the second threshold is the same as the first threshold.

21. The method of claim 14, wherein the characteristic associated with the flow of gas is a Maximum Average Inspiratory Flow (Qave(max)), and wherein controlling the delivery of the flow of gas to the patient comprises comparing the Qave(max) to the first threshold and the second threshold.

22. The method of claim 13, wherein the characteristic associated with the flow of gas is a tidal volume, and wherein controlling the delivery of the flow of gas to the patient comprises comparing the tidal volume to the first threshold and the second threshold.

23. The method of claim 13, wherein the characteristic associated with the flow of gas is a minute ventilation, and wherein controlling the delivery of the flow of gas to the patient comprises comparing the minute ventilation to the first threshold and the second threshold.

24. A system for ventilating a patient, the system comprising:
 means for generating a flow of gas;
 means for delivering the flow of gas to an airway of a patient via a patient circuit;
 means for generating output signals related to a characteristic associated with the flow of gas; and
 means for selectively controlling delivery of the flow of gas to the patient, wherein flow into the patient is positive and the flow out of the patient is negative flow, by:
  1) operating in a first pressure mode responsive to the characteristic being below a first threshold, wherein the first pressure mode comprises providing the gas to the patient at a first inspiratory pressure during inspiration and a first expiratory pressure during expiration, and wherein the first inspiratory pressure is higher than the first expiratory pressure; and
  2) operating in a second pressure mode responsive to the characteristic being above a second threshold, wherein the second pressure mode comprises providing the gas to the patient at a second inspiratory pressure during inspiration and a second expiratory pressure during expiration, wherein the second expiratory pressure is higher than the second inspiratory pressure, and the means for selectively controlling delivery of the flow of gas to the patient is configured such that the first inspiratory pressure is a first inspiratory positive airway pressure (IPAP) level and the first expiratory pressure is a first expiratory positive airway pressure (EPAP) level, and wherein the first IPAP level is higher than the first EPAP level in the first pressure mode; and wherein the second inspiratory pressure is a second IPAP level and the second expiratory pressure is a second EPAP level, and wherein the second EPAP level is higher than the second IPAP level in the second pressure mode; and whereby the first IPAP, first EPAP, second IPAP, and second EPAP are positive gas pressure in a flow direction towards the patient.

25. The system of claim 24, wherein the means for selectively controlling delivery of the flow of gas to the patient is configured to detect a predetermined breathing characteristic of the patient based on the characteristic associated with the flow of gas, wherein the means for controlling operates in the second pressure mode responsive to detection of the predetermined breathing characteristic and the characteristic associated with the flow of gas being above the second threshold.

* * * * *